United States Patent [19]

Stahly

[11] Patent Number: 5,189,208
[45] Date of Patent: Feb. 23, 1993

[54] IBUPROFEN RESOLUTION

[75] Inventor: G. Patrick Stahly, Baton Rouge, La.

[73] Assignee: Ethyl Corporation, Richmond, Va.

[21] Appl. No.: 724,166

[22] Filed: Jul. 1, 1991

[51] Int. Cl.$^5$ .............................................. C07B 57/00
[52] U.S. Cl. .................................... 562/402; 562/460; 562/466
[58] Field of Search .................. 562/402, 466, 460

[56] References Cited

U.S. PATENT DOCUMENTS

| | | | |
|---|---|---|---|
| 4,417,070 | 11/1983 | Arai et al. | 560/56 |
| 4,786,731 | 11/1988 | Russell | 544/354 |
| 4,865,770 | 9/1989 | Piselli | 562/402 |
| 4,983,765 | 1/1991 | Lukas et al. | 562/401 |

OTHER PUBLICATIONS

Jaques et al., *Enantiomers, Racemates and Resolutions*, pp. 193-196, John Wiley and Sons, Inc., New York (1981).

Sheldon, *Chemistry & Industry*, Apr. 2, 1990, pp. 212-219.

*Primary Examiner*—José G. Dees
*Assistant Examiner*—Vera C. Clarke
*Attorney, Agent, or Firm*—Richard J. Hammond

[57] ABSTRACT

A process for obtaining a substantially pure enantiomer of ibuprofen is described. The process utilizes first an enantiomerically enriched mixture of ibuprofen obtained from kinetic resolution, diastereomeric crystallization or asymmetric synthesis processes. This enriched mixture is dissolved in a solvent and solid racemic ibuprofen is separated, leaving a mother liquid comprising the solvent and the enriched enantiomer substantially free of the other enantiomer.

9 Claims, No Drawings

IBUPROFEN RESOLUTION

FIELD OF THE INVENTION

This invention relates to a process for obtaining a highly pure enantiomer of ibuprofen from a mixture of enantiomers.

BACKGROUND OF INVENTION

The resolution of racemates constitutes the main method for industrial preparation of pure enantiomers. Methods for such resolution include: direct preferential crystallization; crystallization of the diastereomeric salts; kinetic resolution; and asymmetric synthesis.

Also referred to as resolution by entrainment, preferential crystallization is widely used on an industrial scale; for example, in the manufacture of α-methyl-L-dopa and chloramphenicol. It is technical feasible only with racemates which are so-called conglomerates and consist of mechanical mixtures of crystals of the two enantiomers. Unfortunately, less than 20 percent of all racemates are conglomerates. The rest are true racemic compounds which cannot be separated by preferential crystallization (i.e., by seeding with the crystals of one enantiomer). A conglomerate exhibits a minimum melting point for the racemic mixture while a racemic compound shows a maximum melting point. The success of preferential crystallization depends on the fact that the two enantiomers crystallize at different rates and on the correlation between the melting point diagram and the solubility phase diagram, i.e., the mixture having the lowest melting point is the most soluble, and for a conglomerate this is the racemic mixture. Ibuprofen is a true racemic compound.

If the racemate is a true racemic compound, a homogeneous sold phase of the two enantiomers co-existing in the same unit cell, it may be separated via diastereomer crystallization, this generally involves reaction of the racemate with an optically pure acid or base (the resolving agent) to form a mixture of diastereomeric salts which is separated by crystallization.

Diastereomer crystallization is widely used for the industrial synthesis of pure enantiomers. A typical example is the Andeno process for the manufacture of (D)-(−)-phenylglycine, an antibiotic intermediate, using optically pure camphor sulfonic acid as the resolving agent.

The theoretical once-through yield of a resolution via diastereomer crystallization is 50 percent. However, in practice, a single recrystallization produces a composition that is simply an enantiomerically enriched racemate.

Another method for the resolution of racemates is kinetic resolution, the success of which depends on the fact that the two enantiomers react at different rates with a chiral addend.

Kinetic resolutions can also be effected using chiral metal complexes as chemocatalysts, e.g., the enantioselective rhodium-BINAP-catalyzed isomerization of the chiral allylic alcohol to the analogous prostaglandin intermediates reported by Noyori.

The enantioselective conversion of a prochiral substrate to an optically active product, by reaction with a chiral addend, is referred to as an asymmetric synthesis. From an economic viewpoint, the chiral addend functions in catalytic quantities. This may involve a simple chemocatalyst or a biocatalyst. An example of the former is the well-known Monsanto process for the manufacture L-dopa by catalytic asymmetric hydrogenation. See Knowles, et al., *J. Am. Chem. Soc.*, 97, 2567 (1975). An example of the latter is the Genex process for the synthesis of L-phenylalanine by the addition of ammonia to transcinnamic acid in the presence of L-phenylalanine ammonia lyase (PAL). See Hamilton et al., *Trends in Biotechnology*, 3, 64–68, (1985).

With the exception of the preferential crystallization process, when applied to ibuprofen the prior art processes typically produce a first mixture that is essentially an enantiomerically enriched racemic composition. A number of crystallizations are required to yield the substantially pure enantiomer.

OBJECTS OF THE INVENTION

It is an object of the present invention to provide a process for obtaining a substantially pure enantiomer of ibuprofen.

It is a further object of the present invention to obtain such substantially pure enantiomer from compositions of enantiomerically enriched racemic ibuprofen.

PREFERRED EMBODIMENTS OF THE INVENTION

The objective of the present invention is achieved by dissolving an enantiomerically enriched racemic mixture of ibuprofen in an inert solvent. Any solvent that is not reactive with ibuprofen and dissolves substantially all of the mixture is acceptable. Thus, various aliphatic hydrocarbon solvents, i.e., hexane, heptane, octane, etc., aromatic hydrocarbon solvents, i.e., benzene, toluene, xylene, and alcohol solvents, i.e., methanol, ethanol, 1-propyl aloohol, etc., are preferred for such solvent. Particularly preferred are the aliphatic hydrocarbon solvents, especially hexane.

Upon evaporation of some of the solvent or cooling of the solution, a solid crystalline material separates. The solid is racemic ibuprofen. Of course, other standard, well known methods can also be used to obtain the precipitated, solid racemic material, e.g., adding a non-solvent to the solution. The desired end result, however, is to produce and separate from the mother liquor a solid that is essentially the crystalline form of racemic ibuprofen. The mother liquor remains and comprises the solvent and the enriched enantiomer substantially free of any of the other enantiomer of the ibuprofen racemate.

The solid crystalline racemic ibuprofen is separated from the mother liquor by any conventional method (centrifugation, filtration, decantation, etc.) The liquid remaining, the mother liquor, can then be partially evaporated or cooled or treated in any conventional manner to cause the enantiomer to precipitate.

The precipitated product is substantially pure enantiomeric material. However, it should be understood that the actual purity of such "substantially pure enantiomer" is dependent on the composition of the starting enantiomerically enriched racemic ibuprofen. Thus, by carrying out the process of this invention using ibuprofen having a composition of 76% of the S(+) enantiomer (a 26% enriched racemic composition), the process of this invention yields the substantially pure enantiomer, i.e., a 94% S(+) pure product. Compositions of greater enrichment in, for example, the S(+) isomer yield final product of even higher purity, i.e., an 80% S(+) composition produces the substantially pure enantiomer as a 97% S(+) pure product. Of course, compositions having smaller amounts of enrichment than the above noted 76% S(+) produce final product of less than 94% S(+). The relationship between composition of the starting ibuprofen and composition of the final ibuprofen is surprisingly linear. The process of this invention provides, in one step, a product that is obtained by the prior art processes mentioned earlier in numerous steps. As such, the process provides a more simplified method of obtaining highly pure enantiomers of ibuprofen than previously available.

The following example is for illustration only and is not intended as limiting the invention in any way.

EXAMPLE

From an asymmetric synthesis procedure was obtained 4.8 g of ibuprofen consisting of 76% S isomer and 24% R isomer. This was recrystallized from about 10 mL of hexane. The crystal crop was removed by filtration to give 1.9 g of ibuprofen consisting of 55% S isomer and 45% R isomer. Concentration of the mother liquid afforded 2.5 g of solid ibuprofen consisting of 94% S isomer and 4% R isomer. Isomer compositions were determined by high pressure liquid chromatography using a chiral stationary phase.

I claim:

1. A process for producing a substantially pure enantiomer of ibuprofen, comprising forming a solution of an enantiomerically enriched racemic ibuprofen with an inert solvent;

separating from said solution solid racemic ibuprofen and forming a mother liquor comprising the inert solvent and the substantially pure enantiomer; and precipitating the substantially pure enantiomer from the mother liquor.

2. The process of claim 1 wherein the enantiomerically enriched racemic ibuprofen is obtained from a disatereomeric crystallization process.

3. The process of claim 1 wherein the enantiomerically enriched racemic ibuprofen is obtained from a catalyzed kinetic resolution process.

4. The process according to claim 3 wherein said catalyzed kinetic resolution process is carried out with a chemical catalyst.

5. The process according to claim 3 wherein said catalyzed kinetic resolution process is carried out with a biological catalyst.

6. The process according to claim 1 wherein said enantiomerically enriched racemic ibuprofen is obtained from a catalyzed asymmetric synthesis.

7. The process according to claim 6 wherein the catalyst is a chemical catalyst.

8. The process according to claim 6 wherein the catalyst is a biological catalyst.

9. The process of claim 1 wherein said substantially pure enantiomer of ibuprofen is S-(+)-ibuprofen.

* * * * *